United States Patent [19]

Scheuermann et al.

[11] 4,133,828
[45] Jan. 9, 1979

[54] MANUFACTURE OF DIMETHYLAMINOBENZENESULFONATES

[75] Inventors: Horst Scheuermann, Ludwigshafen; Helmut Hoch, Wachenheim, both of Fed. Rep. of Germany

[73] Assignee: BASF Aktiengesellschaft, Ludwigshafen, Fed. Rep. of Germany

[21] Appl. No.: 707,867

[22] Filed: Jul. 22, 1976

[30] Foreign Application Priority Data

Aug. 28, 1975 [DE] Fed. Rep. of Germany ....... 2538307

[51] Int. Cl.² .................. C07C 143/56; C07C 143/68
[52] U.S. Cl. .................................................. 260/508
[58] Field of Search ............... 260/508, 509, 510, 580, 260/581

[56] References Cited

U.S. PATENT DOCUMENTS

| | | | |
|---|---|---|---|
| 2,322,572 | 6/1943 | Fisher | 260/508 |
| 2,784,220 | 3/1957 | Spiegler | 260/510 |
| 3,328,465 | 6/1967 | Spiegler | 260/508 |

OTHER PUBLICATIONS

Pearson, et al., J. Amer. Chem. Soc., vol. 73, p. 864.

*Primary Examiner*—James O. Thomas, Jr.
*Assistant Examiner*—Werren B. Lone
*Attorney, Agent, or Firm*—Keil, Thompson & Shurtleff

[57] ABSTRACT

Dimethylaminobenzenesulfonates are manufactured by reacting nitrobenzenesulfonates with formaldehyde and hydrogen in the presence of a hydrogenation catalyst containing a metal of atomic number from 24 to 29 and of phosphoric acid and water at a pH of from 2 to 3.5, at from 50 to 150° C, under a pressure of at least 40 bars, with a residence time of from 1 to 15 minutes. The products are starting materials for the synthesis of dyes, especially of rhodamine dyes, oxazine dyes and reactive dyes, and also of pharmaceuticals and pesticides.

14 Claims, No Drawings

MANUFACTURE OF DIMETHYLAMINOBENZENESULFONATES

The invention relates to a process for the manufacture of dimethylaminobenzenesulfonates by reaction of nitrobenzenesulfonates with formaldehyde and hydrogen in the presence of a hydrogenation catalyst containing a metal of atomic number from 24 to 29 and of phosphoric acid, at from 50 to 150° C., under a pressure of at least 40 bars and with a residence time of from 1 to 15 minutes.

Aust. J. Chem., 23 (1970), 204, in conjunction with J. Amer. Chem. Soc., 73 (1951), 864, discloses that methyl m-dimethylaminobenzoate can be manufactured by reductive methylation of methyl m-nitrobenzoate with hydrogen and formaldehyde in ethyl alcohol in the presence of hydrochloric acid and of a pre-reduced Adams catalyst at 5° C. under a pressure of 45 psi. The second of the above publications points out that reductive methylation is rarely used for the manufacture of tertiary aromatic amines, since condensation of the starting compounds easily occurs, and recommends solely the above procedure. The Australian publication does not state the yield of ester manufactured by this method. German Laid-Open Application DOS 2,329,553 points out that the process cannot be carried out on an industrial scale since the yield of end product is poor. Since the ultimate use of methyl 3-dimethylaminobenzoate and of 3-dimethylaminobenzoic acid requires high purity, the said Laid-Open Application teaches that the isolation of the end product is expensive and that the process is therefore economically unsatisfactory.

German Pat. No. 716,668 discloses that the reductive methylation of aminobenzoic acid derivatives also demands that special conditions be observed. It is true that secondary amines can be obtained with other catalysts, eg. nickel on kieselguhr, using additional catalysts such as piperidine, eg. ethyl isobutylaminobenzoate can be obtained from ethyl p-aminobenzoate and isobutyraldehyde. To manufacture tertiary amines. eg. p-N-dimethylaminobenzamide or ethyl N-dimethylaminobenzoate, from the corresponding primary amines by reductive methylation, platinum catalysts are used, as shown by Examples 12 and 15, in the presence of hydrochloric acid at 20° C. and 3.5 atmospheres gauge pressure. The yields of end product are not stated.

The use of palladium on active charcoal, in the presence of acetic acid or in an ethanolic solution of the reactants, if appropriate together with sodium acetate, as a catalyst for the reductive methylation of nitrobenzoic acids at room temperature and under atmospheric pressure has also been disclosed (J. Chem. Soc. 1950, 1,342 et seq.). Freifelder, Practical Catalytic Hydrogenation (Wiley, N.Y. (1971), pages 346 et seq.) discloses that depending on the starting material and on the chosen substituents, specific catalysts and reaction conditions must be selected. For the case of the reductive methylation of 4-aminobenzoic acid, platinum oxide is specifically recommended as the catalyst; the publication shows that the dimethylamino compound can be produced in significant yield only if hydrochloric acid is present (376).

Organic Reactions, volume IV, page 194 (Wiley, N.Y., 1948) discloses that aromatic amines which do not have substituents in the o- and p-position resinify on treatment with formaldehyde in acid solution. Aromatic nitro compounds can only by reacted with hydrogen and aldehydes, in the presence of platinum catalysts and acetic acid, to give dialkylarylamines if the aldehyde used is not formaldehyde.

German Laid-Open Application DOS 2,329,553 discloses a process for the manufacture of dimethylaminobenzoates by reaction of nitrobenzoic acid esters with formaldehyde and hydrogen in the presence of a hydrogenation catalyst which contains one or more metals of atomic number from 24 to 29, and of weak organic acids, at from 35 to 150° C. and under a pressure of at least 40 atmospheres. According to the said German Laid-Open Application, it is specifically the use of weak organic acids, which in general have a dissociation constant of not more than $1.5 \times 10^{-4}$, preferably from $1.5 \times 10^{-4}$ to $1 \times 10^{-6}$, which is essential for the process to give good results. The reaction mixtures accordingly have a pH of from 4 to 6, especially from 4 to 5. Residence times of from 15 to 600 minutes are quoted. If this process is carried out with the alkali metal salts of nitrobenzenemonosulfonic acids as starting materials, in the presence of weak organic acids or of hydrochloric acid or sulfuric acid — a variant which has not previously been disclosed — heterogeneous mixtures of numerous constituents, and no significant yield of dimethylaminobenzene compounds, are obtained.

U.S. Pat. No. 2,784,220 discloses the hydrogenation of disodium 4,4'-dinitrostilbene-2,2'-disulfonate at 1 atmosphere, from 70 to 90° C. and a pH of from 5.6 to 7, in the presence of platinum or palladium catalysts, using reaction times of about 4 hours.

All these processes are unsatisfactory, particularly on an industrial scale, with respect to simple and economical operation, yield and space-time yield of end product, and economical use of the catalyst. The use of hydrochloric acid entails corrosion problems. In some cases, long reaction times are needed in order to obtain a significant yield of end product.

It is an object of the present invention to provide a new process whereby alkali metal salts of dimethylaminobenzenesulfonic acids can be manufactured more simply and more economically, and with better yield, higher purity and better space-time yield.

We have found that this object is achieved and that dimethylaminobenzenesulfonates of the formula

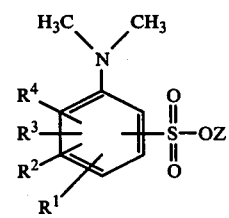

I where $R^1$, $R^2$, $R^3$ and $R^4$ may be identical or different and each is hydrogen or an aliphatic radical and Z is an alkali metal atom are obtained in an advantageous manner by reaction of nitrobenzene compounds with formaldehyde and hydrogen in the presence of hydrogenation catalysts, when nitrobenzenesulfonates of the formula

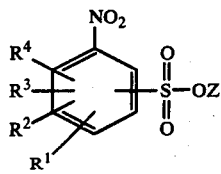

where $R^1$, $R^2$, $R^3$, $R^4$ and Z have the above meanings, are reacted with formaldehyde and hydrogen in the presence of a hydrogenation catalyst which contains one or more metals of atomic number from 24 to 29, at from 50 to 150° C. and a pressure of not less than 40 bars, in the presence of phosphoric acid and water, at a pH of from 2 to 3.5, and using a reaction time of from 1 to 15 minutes.

The following equation represents the reaction when sodium 3-nitrobenzenesulfonate is used:

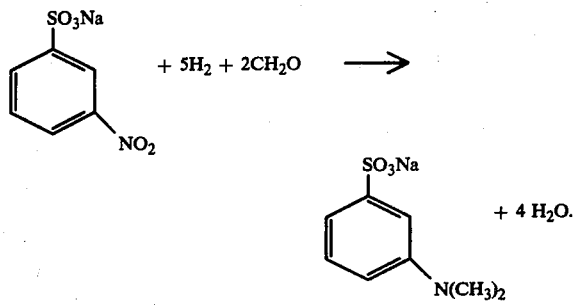

Compared to the conventional processes, the process according to the invention gives alkali metal salts of dimethylaminobenzenesulfonic acids in a simple and more economical manner and in better yield, higher purity and better spaced-time yield. The process does not require expensive catalysts and can also be used industrially. It avoids corrosion problems. All these advantageous results are surprising in view of the prior art. Furthermore, it had to be assumed that under the reaction conditions the sulfonate compounds would also form by-products. In view of the short residence times and the low pH, and in view of the prior art, it had to be expected that the mixtures obtained would contain numerous constituents and/or that the yields of end product would be substantially lower.

The starting materials used are nitrobenzenesulfonates which in addition to the nitro group and a sulfonate group have not more than four and preferably zero, 1 or 2 substituents on the benzene nucleus; compounds which have the sulfonate group in the m- or p-position and may have a further substituent in the m- or p-position to the nitro group are preferred. Preferred starting materials II, and accordingly preferred end products I, are those in which $R^1$, $R^2$, $R^3$ and $R^4$ are identical or different and each is hydrogen or alkyl of 1 to 6 carbon atoms and Z is potassium and especially sodium. The above radicals may be substituted by organic groups and/or atoms which are inert under the reaction conditions, eg. alkyl or dialkylamino, in each of which alkyl is of 1 to 4 carbon atoms.

Examples of suitable starting materials II are the potassium salt and especially the sodium salt of nitrobenzene-o-sulfonic acid and especially of nitrobenzene-m-sulfonic acid and nitrobenzene-p-sulfonic acid; corresponding sulfonates substituted by methyl, ethyl, n-propyl, isopropyl, n-butyl, isobutyl, sec.-butyl, tert.-butyl, pentyl, pent-2-yl, pent-3-yl or n-hexyl in the o-position or especially in the m-position relative to the nitro group; and nitrobenzenesulfonates in which the 2-, 3- and 4-positions, 2-, 3- and 5-positions, 2-, 3- and 6-positions, 3-, 4- and 5-positions, 2-, 4- and 6-positions, 2-, 3-, 4- and 5-positions, 2-, 3-, 5- and 6-positions or 2-, 3-, 4- and 6-positions are occupied simultaneously, by the sulfonate group and by identical or different substituents from amongst those mentioned above.

Formaldehyde may be used as a gas, as a solution in an alcohol, eg. in methanol, or, preferably, as an aqueous solution, advantageously of from 30 to 40 percent strength by weight. The starting material II can be reacted with a stoichiometric amount or an excess of formaldehyde, preferably using a ratio of from 2 to 8 moles, especially of from 2 to 3 moles, of formaldehyde per mole of starting material II.

The reaction is carried out at from 50 to 150° C., preferably from 60 to 90° C. and especially from 70 to 80° C., and under a pressure of not less than 40 bars, preferably from 70 to 350 bars, advantageously from 100 to 300 bars and especially from 100 to 250 bars, batchwise or, as a rule, preferably continuously. Water is always present in the reaction, preferably in an amount of from 300 to 5,000 percent by weight, especially from 800 to 1,500 percent by weight, based on starting material II. If appropriate, organic solvents which are inert under the reaction conditions, eg. alkanols, especially of 1 to 4 carbon atoms, such as methanol, ethanol and isopropanol, glycols, glycol ethers, eg. methylethylene glycol, tetrahydrofuran or mixtures of the said solvents with one another and/or with water are used, advantageously in amounts of from 100 to 5,000 percent by weight, especially from 500 to 1,500 percent by weight, of organic solvent, based on starting material II.

The reaction is carried out in the presence of phosphoric acid. This may consist of metaphosphoric acid, pyrophosphoric acid or, in particular, orthophosphoric acid, advantageously in the form of an aqueous solution containing from 2 to 60, preferably from 7 to 20, percent by weight of phosphorus pentoxide. The phosphoric acid may also be in the form of a polyphosphoric acid, eg. containing from 72 to 88 percent by weight of $P_2O_5$, and equally it is possible to use phosphoric acid of the above concentrations together with phosphorus pentoxide, preferably in amounts corresponding to the polyphosphoric acids. The phosphoric acid (assumed for calculation purposes to be orthophosphoric acid, regardless of its actual structure) is in general employed in an amount of from 0.001 to 0.2, preferably from 0.005 to 0.15, mole of acid, per mole of starting material II. The phosphoric acid may also be contained entirely or partially in the hydrogenation catalyst. The reaction is carried out at a pH of from 2 to 3.5, preferably from 2.5 to 3.2.

The hydrogenation catalysts are, in general, one or more metals of atomic number from 24 to 29, preferably cobalt, copper, manganese and/or nickel catalysts, eg. sintered catalysts of this type. The metals may be present in the catalyst in the form of their oxides and/or as mixtures with phosphoric acid. Advantageous catalysts of the said type contain from 3 to 30 percent by weight of copper and/or cobalt, from 0.5 to 10 percent by weight of manganese and from 10 to 80 percent by weight of nickel. If appropriate, from 0.1 to 5 percent by weight of phosphoric acid, based on the amount of metal, may also be present in the catalyst.

The amount of hydrogenation catalyst used for the reaction is as a rule from 0.5 to 50, preferably from 2 to 30, percent by weight, and in the case of Raney nickel preferably from 2 to 5 percent by weight, based on starting material II. The catalyst may be used as a mixture with a carrier suitable for the reaction, eg. silicon dioxide, and as a rule the amount of the catalyst is from 10 to 40 percent by weight of the mixture of catalyst and carrier. Examples of suitable catalyst mixtures are:

a) 70.5% of Ni, 19.7% of Co, 5.4% of Mn and 4.2% of phosphoric acid.
b) 15% of Ni, 6.1% of Cu, 1.5% of Mn and 0.9% of phosphoric acid on $SiO_2$.
c) 15% of Ni, 5.2% of Cu and 1.3% of Mn on $SiO_2$.

The use of Raney nickel is particularly advantageous. As a rule, the amounts of hydrogen introduced into the reaction mixture at the start, and during the reaction, are such that an appropriate reaction pressure, suitably from 40 to 150 bars, is set up at the reaction temperature. It is preferred to use from 5 to 10 moles of $H_2$, based on starting material II. Inert gases such as nitrogen may also be used for appropriately adjusting the pressure.

The residence times in the reaction chamber are from 1 to 15 minutes, preferably from 5 to 12 minutes.

The reaction may be carried out as follows: the starting material II, advantageously dissolved in water, and the aldehyde, if appropriate together with the organic solvent, are introduced into a reactor, the catalyst and the acid are added and the reaction chamber is flushed with nitrogen. Hydrogen is then injected until the above reaction pressure is reached. The reaction mixture is now brought to the above temperature and is kept thereat, and at the above pH, for the duration of the residence time, with introduction of further hydrogen, until the reaction no longer consumes hydrogen. The reaction mixture is then cooled and filtered. The end product is isolated from the filtrate by conventional methods, eg. by crystallization. The end product can also be isolated by evaporating the filtrate to dryness; alternatively, the organic solvent and/or a part of the water is distilled off until the solution contains from about 40 to 50 percent by weight of the alkali metal salt of the dimethylaminobenzenesulfonic acid, and this solution is used to carry out the fusion with alkali, so as to give the dimethylaminophenol.

A particularly preferred embodiment of the reaction is the following continuous method: an aqueous or, preferably, aqueous-methanolic solution (weight ratio of water:methanol = from 1 to 10:1), which advantageously contains 10 percent by weight of the alkali metal salt of the nitrobenzene sulfonic acid II and also contains formaldehyde and phosphoric acid and has been pre-heated to about 70° C., is fed into a hydrogenation reactor. The hydrogenation reactor is preferably a vertical cylindrical high pressure tube and is filled with the catalyst. The solution is charged in together with hydrogen. After it has passed through the catalyst, the reaction solution is discharged at the other end of the reactor. A part of the reaction solution is advantageously recycled, by means of a circulation pump, to the reactor inlet, in order to remove the heat of reaction, whilst the other part of the reaction solution is discharged from the pressure system and the end product is isolated from it by the above method.

The compounds which may be manufactured by the process of the invention are valuable starting materials for the synthesis of dyes, especially of rhodamine dyes, oxazine dyes and reactive dyes, and also of pharmaceuticals and pesticides. Thus, eg., substituted or unsubstituted dimethylamino-m-benzenesulfonates can be converted, by fusion with alkali using the method described in Ullmanns Encyklopädie der technischen Chemie, volume 3, page 473, to the corresponding dimethyl-m-aminophenols which are used for the manufacture of the above rhodamine dyes and of rosamine dyes.

In the Examples, parts are by weight and bear the same relation to parts by volume as that of the kilogram to the liter.

EXAMPLE 1

Sodium 3-dimethylaminobenzenesulfonate

The hydrogenation reactor used is a vertical cylindrical high pressure tube having a capacity of 1,000 parts by volume and a length: diameter ratio of 45:1. The reactor is filled with 670 parts of a catalyst which consists of 15 percent by weight of nickel, 5.2 percent by weight of copper and 1.3% by weight of manganese, on silica as the carrier.

A solution, heated to 70° C., of 90 parts of sodium 3-nitrobenzenesulfonate, 108 parts of an aqueous 30 percent strength by weight formaldehyde solution, 7 parts of a 10 percent strength by weight phosphoric acid, 390 parts of methanol, 390 parts of water and 4,000 parts of fluid crude reaction mixture (containing 345 parts of end product, 112 parts of 30 percent strength by weight formaldehyde solution, 28 parts of 10 percent strength by weight phosphoric acid, 1,565 parts of methanol and 1,950 parts of water), which is recycled from the bottom of the reactor by means of a circulation pump, are pumped in, per hour, together with hydrogen, at the top of the reactor. A pressure of 250 bars and a temperature of from 75 to 80° C. is maintained in the reactor. The pH is 3.1 and the residence time is 12 minutes.

1,000 parts of reaction solution per hour are branched off at the bottom of the reactor, and the methanol is distilled off in a distillation unit.

The hourly yield is 86 parts of sodium 3-dimethylaminobenzenesulfonate (96% of theory, based on nitro compound employed) of melting point 330–340° C. (with decomposition).

EXAMPLE 2

Sodium 4-dimethylamino-2-methylbenzenesulfonate

Using the method described in Example 1, a solution heated to 70° C., of 70 parts of sodium 4-nitro-2-methylbenzenesulfonate, 90 parts of an aqueous 30 percent strength by weight formaldehyde solution, 9 parts of a 12 percent strength by weight phosphoric acid, 410 parts of water, 420 parts of methanol and 7,000 parts of fluid crude reaction mixture (containing 455 parts of end product, 217 parts of an aqueous 30 percent strength by weight formaldehyde solution, 63 parts of 12 percent strength by weight phosphoric acid, 2,940 parts of methanol and 3,325 parts of water), which is recycled by means of a circulation pump at the bottom of the reactor, are pumped in, per hour, together with hydrogen, at the top of the reactor. The catalyst used corresponds to that described in Example 1. A pressure of 250 bars and a temperature of from 75 to 80° C. is maintained in the reactor. The pH is 3.0. The residence time is 7 minutes. Per hour, 1,000 parts of reaction product are taken from the reactor. The hourly yield is 63 parts of sodium 4-dimethylamino-2-methylbenzenesulfonate (95% of theory, based on nitro compound employed) of melting point 310–315° C. (with decomposition).

We claim:

1. A process for the manufacture of dimethylaminobenzenesulfonates of the formula

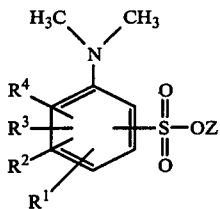

I where $R^1$, $R^2$, $R^3$ and $R^4$ may be identical or different and each is hydrogen or alkyl of 1 to 6 carbon atoms and Z is an alkali metal atom, which process comprises reacting a nitrobenzenesulfonate of the formula

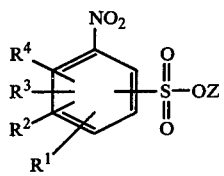

II where $R^1$, $R^2$, $R^3$, $R^4$ and Z have the above meanings, with formaldehyde and hydrogen in the presence of a hydrogenation catalyst consisting essentially of one or more metals of atomic number from 24 to 29 or their oxides, at from 50 to 150° C. and a pressure of not less than 40 bars, in the presence of phosphoric acid and water, at a pH of from 2 to 3.5, and using a reaction time of from 1 to 15 minutes.

2. A process as claimed in claim 1, wherein the reaction is carried out using a ratio of from 2 to 8 moles of formaldehyde per mole of starting material II.

3. A process as claimed in claim 1, wherein the reaction is carried out at from 60 to 90° C.

4. A process as claimed in claim 1 wherein the reaction is carried out at from 70 to 80° C.

5. A process as claimed in claim 1, wherein the reaction is carried out under a pressure of from 70 to 350 bars.

6. A process as claimed in claim 1, wherein the reaction is carried out under a pressure of from 100 to 300 bars.

7. A process as claimed in claim 1, wherein the reaction is carried out using from 300 to 5,000 percent by weight of water, based on starting material II.

8. A process as claimed in claim 1, wherein the reaction is carried out using organic solvents which are inert under the reaction conditions.

9. A process as claimed in claim 1, wherein the reaction is carried out using from 0.001 to 0.2 mole of phosphoric acid per mole of starting material II.

10. A process as claimed in claim 1, wherein the reaction is carried out at a pH of from 2.5 to 3.2.

11. A process as claimed in claim 1, wherein the reaction is carried out using from 0.5 to 50 percent by weight of hydrogenation catalyst, based on starting material II.

12. A process as claimed in claim 1, wherein the reaction is carried out using a hydrogenation catalyst in which the metal is cobalt, copper, manganese and/or nickel.

13. A process as claimed in claim 1, wherein the reaction is carried out using from 5 to 10 moles of $H_2$, based on starting material II.

14. A process as claimed in claim 1, wherein the reaction is carried out using residence times, in the reaction chamber, of from 5 to 12 minutes.

* * * * *